(12) United States Patent
Dyballa et al.

(10) Patent No.: US 9,751,904 B2
(45) Date of Patent: Sep. 5, 2017

(54) METHOD FOR REDUCING THE CHLORINE CONTENT OF ORGANOMONOPHOSPHITES USING DIMETHYLAMINOBUTANE, TRIETHYLAMINE OR TRIETHANOLAMINE

(71) Applicant: EVONIK DEGUSSA GMBH, Essen (DE)

(72) Inventors: Katrin Marie Dyballa, Recklinghausen (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/312,024

(22) PCT Filed: Apr. 29, 2015

(86) PCT No.: PCT/EP2015/059290
§ 371 (c)(1),
(2) Date: Nov. 17, 2016

(87) PCT Pub. No.: WO2015/176929
PCT Pub. Date: Nov. 26, 2015

(65) Prior Publication Data
US 2017/0088570 A1  Mar. 30, 2017

(30) Foreign Application Priority Data

| May 20, 2014 | (DE) | 10 2014 209 532 |
| May 20, 2014 | (DE) | 10 2014 209 533 |
| May 20, 2014 | (DE) | 10 2014 209 534 |
| May 20, 2014 | (DE) | 10 2014 209 535 |
| May 20, 2014 | (DE) | 10 2014 209 536 |
| Feb. 16, 2015 | (DE) | 10 2015 202 722 |

(51) Int. Cl.
*C07F 9/145* (2006.01)
(52) U.S. Cl.
CPC .................. *C07F 9/145* (2013.01)
(58) Field of Classification Search
CPC ....................................................... C07F 9/145
See application file for complete search history.

(56) References Cited

U.S. PATENT DOCUMENTS

| 4,835,299 A | 5/1989 | Maher et al. |
| 2008/0076944 A1 | 3/2008 | Bartsch et al. |
| 2013/0317246 A1 | 11/2013 | Kreidler et al. |

FOREIGN PATENT DOCUMENTS

| CA | 2862041 A1 | 7/2013 | |
| DE | 10 2004 049 339 A1 | 4/2006 | |
| DE | 10 2011 002 640 A1 | 7/2012 | |
| EP | 0 285 136 A2 | 10/1988 | |
| WO | 01/21579 A1 | 3/2001 | |
| WO | 2013/098368 A1 | 7/2013 | |
| WO | WO 2013/098368 * | 7/2013 | ............ C07F 9/6574 |

OTHER PUBLICATIONS

International Search Report for PCT/EP2015/059290 dated Nov. 26, 2015 (7 pages).
Written Opinion for PCT/EP2015/059290 dated Nov. 26, 2015 (13 pages).
International Preliminary Report on Patentability for PCT/EP2015/059290 dated Nov. 22, 2016 (15 pages).
Armarego, Wilfred L.F., et al. Purification of Laboratory Chemicals, Butterworth Heinemann (Elsevier), 6th edition, Oxford 2009 (index and chapter abstracts provided).
Harris, Robin K. et al. NMR Nomenclature, Nuclear Spin Properties and Conventions for Chemical Shifts. Pure Appl. Chem., 2001, 73, pp. 1795-1818.
Harris, Robin K. et al. Further Conventions for NMR Shielding and Chemical Shifts. Pure Appl. Chem., 2008, 80, pp. 59-84.
Franke, R., Selent, D., and Börner, A. Applied Hydroformylation. American Chemical Society, ACS Publications, Chemical Reviews, 2012. 5675-5732.
Reetz, M, et al. Helical Triskelion Monophosphites as Ligands in Asymmetric Catalysis. Journal of the American Chemical Society. 2009. 131. 4136-4142.
Sakuma, T. et al. Kinetic resolution of phosphoryl and sulfonyl esters of 1,1'-bi-2-naphthol via Pd-catalyzed alcoholysis of their vinyl ethers. Tetrahedron Asymmetry, 19. 2008. 1593-1599.

\* cited by examiner

*Primary Examiner* — Joseph Kosack
(74) *Attorney, Agent, or Firm* — Smith, Gambrell & Russell, LLP

(57) ABSTRACT

The invention relates to a universally applicable method for reducing the chlorine content of organomonophosphites using dimethylaminobutane or triethylamine.

14 Claims, No Drawings

METHOD FOR REDUCING THE CHLORINE CONTENT OF ORGANOMONOPHOSPHITES USING DIMETHYLAMINOBUTANE, TRIETHYLAMINE OR TRIETHANOLAMINE

The invention relates to a process with universal usefulness for reducing the chlorine content of organomonophosphites, using dimethylaminobutane or triethylamine.

Organophosphorus compounds have gained considerable industrial significance because of their wide range of use. They are used directly as plasticizers, flame retardants, UV stabilizers or as antioxidants. In addition, they are important intermediates in the production of fungicides, herbicides, insecticides and pharmaceuticals.

A specific field of use of the organophosphorus compounds is catalysis:

For instance, especially phosphines, phosphites and phosphoramidites are used as ligands in catalyst complexes, which are used in turn for the homogeneous catalysis of processes operated on an industrial scale. Particular mention should be made of the hydroformylation of unsaturated compounds with carbon monoxide and hydrogen, which generally takes place in the presence of a homogeneous catalyst system which has a metal and at least one organophosphorus compound as ligand.

An introduction to homogeneously catalyzed hydroformylation is given in: B. CORNILS, W. A. HERRMANN: Applied Homogeneous Catalysis with Organometallic Compounds. Vol. 1 & 2, VCH, Weinheim, N.Y., 1996; R. Franke, D. Selent, A. Börner: Applied Hydroformylation. Chem. Rev., 2012, DOI:10.1021/cr3001803.

The synthesis of phosphorous ligands is described repeatedly in the literature. A good overview can be found in "Phosphorous(III) Ligands in Homogeneous Catalysis—Design and Synthesis" by Paul C. J. Kamer and Piet W. N. M. van Leeuwen; John Wiley and Sons, 2012.

In the synthesis of these ligands, chlorine-containing reagents are frequently used. For instance, in the synthesis of phosphite ligands, phosphorus trichloride ($PCl_3$) is usually used.

The chlorine compounds used in the preparation of organophosphorus compounds present many difficulties in the proper use or further processing of the organophosphorus compound:

For instance, the desired organophosphorus compound is never obtained in pure form immediately, and is always obtained in contaminated form as an organophosphorus product which, as well as the desired organophosphorus compound, also contains contaminants. The contaminants are unconverted or incompletely converted reagents, auxiliaries or products from side reactions. In this context, contaminants in the form of chlorine compounds present particular difficulties:

If the chlorine-containing contaminants get into a steel pressure reactor together with the organophosphorus compound used as ligand, the pressure reactor is subject to increased corrosion as a result of the chloride. This is especially true of continuous processes, in which the organophosphorus compounds are metered in over the course of the reaction. This is the case, for example, when the organophosphorus compound is used as a ligand in industrial scale hydroformylation. The metered addition inevitably also results in an accumulation of the secondary components in the reactor. This is critical especially when chloride is one of the secondary components, since chloride attacks even stainless steels (cf. Merkblatt 893 "Edelstahl rostfrei für die Wasserwirtschaft" [Information Sheet 893 "Corrosion-Free Stainless Steel for Water Management"], 1st edition 2007, publisher Informationsstelle Edeistahl Rostfrei, Düsseldorf.)

One important class of organophosphorus compounds is that of the organomonophosphites, or monophosphites for short.

In hydroformylation, these compounds play a prominent part (see R. Franke, D. Selent, A. Börner Applied Hydroformylation. Chem. Rev., 2012, DOI:10.1021/cr3001803).

The chloride content can be determined analytically in a simple manner, for example by aqueous titration. A more extensive determination is that of the total chlorine content, which, as well as the chlorides, also encompasses chlorine bound in other forms. Emphasis on the total chlorine content is also of material relevance, in that it cannot be ruled out that chlorine bound in other forms is also able to damage the reactor. In judging the limits for total chlorine, however, the chloride fraction remains crucial.

The patent literature discloses various methods for reducing the total chlorine content of organophosphorus ligands after the actual synthesis.

WO 2013/098368 A1 describes the purification of organodiphosphites, in which the impurities for removal include not only chloride ions but also, in particular, diols, basic impurities, mono- and dioxides, and also secondary organophosphites. Because of the differences in structural composition and the associated differences in chemical and physical properties such as solubilities between monophosphites and diphosphites, the purification process described in this earlier specification cannot be transposed to the purification of organomonophosphites.

DE 10 2011 002 640 A1 discloses a process for purifying biphephos, a bisphosphite, (6,6'-[(3,3'-di-tert-butyl-5,5'-dimethoxy-1,1'-biphenyl-2,2'-dyl)bis(oxy)]bis(dibenzo[d,f][1,3,2]dioxaphosphepine)).

The process described therein is intended to reduce the chlorine content of biphephos. This is done by washing the biphephos with a solvent selected from ethyl acetate, anisole, ortho-xylene, toluene, acetone, 2-propanol and $C_5$-$C_{10}$-alkanes, or recrystallizing from such a solvent. In this context, however, the long period needed to precipitate or crystallize the product is in need of improvement. The ligand is precipitated overnight, meaning that >8 hours are required. Moreover, it is pointed out in the examples that another solvent has to be added after the precipitation overnight, in order to complement the precipitation (example 2 of DE 10 2011 002 640 A1). These long reaction times are problematic in industrial scale syntheses, since the effect of long residence times and hence ultimately long production times for the ligand is to increase the cost thereof.

Document EP 0 285 136 claims a process for purifying tertiary organophosphites of pentavalent organophosphorus compounds which form as by-products of the synthesis and also as degradation or hydrolysis products of the tertiary organophosphites. The process envisages the treatment of the dissolved contaminated organophosphite with water at elevated temperature in the presence of a Lewis base. Lewis bases used are inorganic salts (carbonates, hydroxides, oxides), tertiary amines and polymers which carry amine groups. One disadvantage of the process described in EP 0 285 136 lies in the treatment with water. Not only the impurities to be removed but also the tertiary organophosphites themselves react under the conditions specified, such that a portion of the product of value is lost according to the hydrolysis stability of the organophosphites. This is particularly critical here, since washing takes place with water, that is, high concentrations are used.

Document DE 10 2004 049 339 describes a process for purifying phosphorous chelate ligands by means of extraction using a polar extractant. The crude ligand was extracted here six times with a polar solvent, and then has a content of amine base, amine hydrochloride or mixtures thereof of less than 100 ppm. In this method of purification, however, enormous amounts of solvent are needed, which is in need of improvement from an economic and ecological point of view.

It was thus an object of the present invention to develop a purifying process for organomonophosphites, in which the chlorine content is reduced, without this process having the above-described disadvantages.

A particular object was for the process to purify organomonophosphites having a chlorine content of more than 1000 ppm to 100 000 ppm and more particularly of 5000 ppm to 100 000 ppm in the organomonophosphite to a chlorine content of less than 1000 ppm in the organomonophosphite. Preferably, the chlorine content was to be reduced to less than 500 ppm in the organomonophosphite, and more preferably to less than 200 ppm in the organomonophosphite. The chlorine contents reported are meant as total chlorine contents.

The total chlorine content is determined by the Wickbold method: Sample preparation according to DIN 51408, and measurement by ion chromatography according to DIN EN ISO 10304.

The contaminated organomonophosphite can contain organic chlorides and/or inorganic chlorides. Organic chlorides contain at least one carbon atom, whereas inorganic chlorides do not include any carbon. Contamination of the organophosphorus product by the following chlorides is particularly likely, since these chlorine-containing compounds are either required in the course of synthesis of organophosphorus compounds or are unavoidably produced as by-products: phosphorus trichloride, chlorophosphites, dichlorophosphites, hydrochlorides of amines, hydrochlorides of alkali metals, chlorides of alkaline earth metals, chlorine-containing acids obtainable from the hydrolysis of phosphorus trichloride. Therefore, the contaminated organomonophosphite generally includes at least one of the chlorides enumerated.

This object is achieved by a process according to claim 1.

A process for reducing the chlorine content in an organomonophosphite of one of the general formulae I, II, III, IV, V, VI, VII, VIII, IX and X:

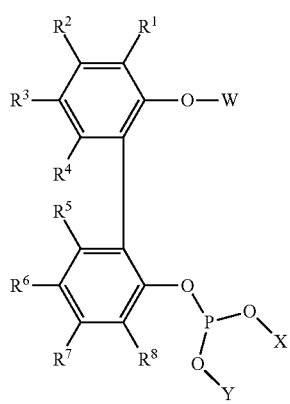
(I)

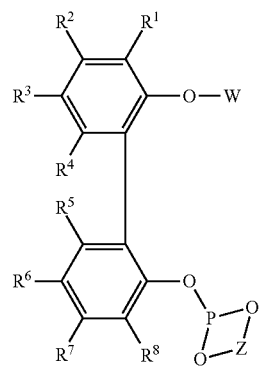
(II)

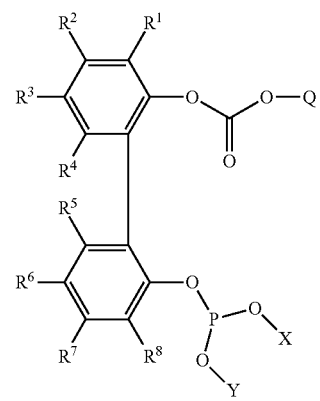
(III)

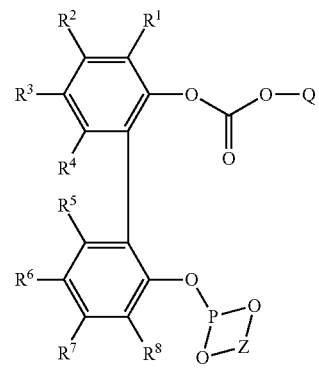
(IV)

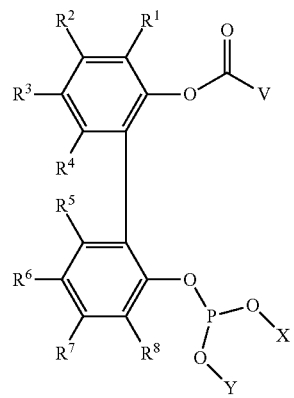
(V)

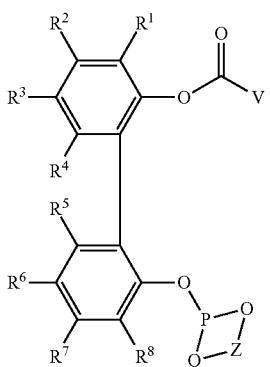 (VI)

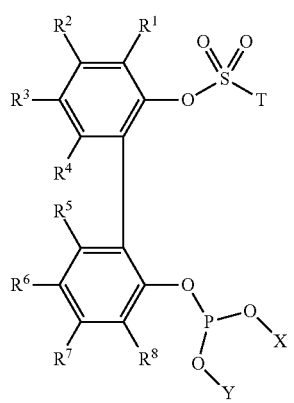 (VII)

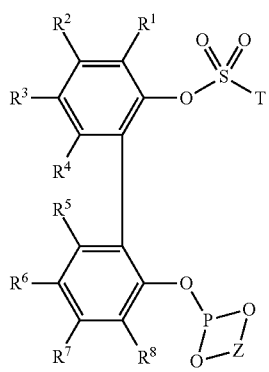 (VIII)

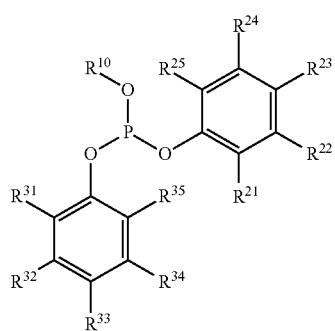 (IX)

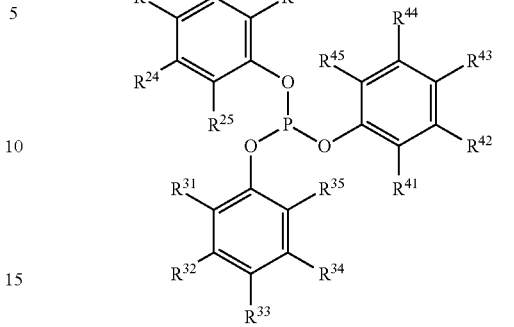 (X)

where the radicals $R^1$, $R^2$, $R^3$, $R^4$, $R^5$, $R^6$, $R^7$, $R^8$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, $R^{45}$ are selected each independently from:

—H, —$(C_1\text{-}C_{12})$-alkyl, —O—$(C_1\text{-}C_{12})$-alkyl, —O—$(C_6\text{-}C_{20})$-aryl, —$(C_6\text{-}C_{20})$-aryl;

and $R^{10}$ is —$(C_1\text{-}C_{12})$-alkyl.

and T is selected from:
—$CH_3$, —$CF_3$, —$CH_2C_6H_5$;

and Q is selected from:
—$(C_1\text{-}C_{12})$-alkyl-, —$C(CH_3)_3$;

and V is selected from:
—$CH_2CH_2COCH_3$, —$C(CH_3)_3$, —$C_6H_5$;

and W is selected from:
-Me, —$CH_2CH_3$, —$CH_2CH_2CH_3$, —$CH_2$-cyclo-$C_3H_5$, —$CH(CH_3)_2$, -cyclo-$C_6H_{11}$, —$C(CH_3)_3$, —$CH_2C_6H_5$, —$CH_2C_6H_3$-2,4-$(CH_3)_2$;

and X and Y are each independently selected from:
—$(C_1\text{-}C_{12})$-alkyl, —$(C_6\text{-}C_{20})$-aryl, —$(C_6\text{-}C_{20})$-aryl-$(C_1\text{-}C_{12})$-alkyl, —$(C_1\text{-}C_{12})$-alkyl-O—$(C_6\text{-}C_{20})$-aryl, and Z is selected from:
—$(C_1\text{-}C_{12})$-alkyl-, —$(C_6\text{-}C_{20})$-aryl-, —$(C_6\text{-}C_{20})$-aryl-$(C_6\text{-}C_{20})$-aryl-;

and the alkyl, cycloalkyl, and aryl groups mentioned may be substituted;

comprising the process steps of:
a) partly or fully dissolving the organomonophosphite in a first solution comprising a first solvent selected from aromatics, alcohols, acetone, ethyl acetate, acetonitrile, ether, water; where the first solution comprises dimethylaminobutane or triethylamine or triethanolamine;
c) the purified organomonophosphite is precipitated.

The dimethylaminobutane, triethylamine and/or triethanolamine suppress unwanted side reactions such as an alcoholysis or a transesterification, for example. Another advantage is that the bound chlorine originally present in the monophosphite dissolves more effectively in the solution by virtue of the dimethylaminobutane present in the solution.

$(C_1\text{-}C_{12})$-Alkyl and O—$(C_1\text{-}C_{12})$-alkyl may each be unsubstituted or substituted by one or more identical or different radicals selected from $(C_3\text{-}C_{12})$-cycloalkyl, $(C_3\text{-}C_{12})$-heterocycloalkyl, $(C_6\text{-}C_{20})$-aryl, fluorine, chlorine, cyano, formyl, acyl and alkoxycarbonyl.

$(C_3\text{-}C_{12})$-Cycloalkyl and $(C_3\text{-}C_{12})$-heterocycloalkyl may each be unsubstituted or substituted by one or more identical or different radicals selected from $(C_1\text{-}C_{12})$-alkyl, $(C_1\text{-}C_{12})$-alkoxy, $(C_3\text{-}C_{12})$-cycloalkyl, $(C_3\text{-}C_{12})$-heterocycloalkyl, $(C_6\text{-}C_{20})$-aryl, fluorine, chlorine, cyano, formyl, acyl and alkoxycarbonyl.

($C_6$-$C_{20}$)-Aryl may each be unsubstituted or substituted by one or more identical or different radicals selected from ($C_1$-$C_{12}$)-alkyl, ($C_1$-$C_{12}$)-alkoxy, ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

In the context of the invention, the expression "—($C_1$-$C_{12}$)-alkyl" encompasses straight-chain and branched alkyl groups. Preferably, these groups are unsubstituted straight-chain or branched —($C_1$-$C_8$)-alkyl groups and most preferably —($C_1$-$C_6$)-alkyl groups. Examples of —($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl-, 3-methylbutyl-, 1,2-dimethylpropyl-, 1,1-dimethylpropyl, 2,2-dimethylpropyl-, 1-ethylpropyl-, n-hexyl-, 2-hexyl-, 2-methylpentyl-, 3-methylpentyl-, 4-methylpentyl-, 1,1-dimethylbutyl-, 1,2-dimethylbutyl-, 2,2-dimethylbutyl-, 1,3-dimethylbutyl-, 2,3-dimethylbutyl-, 3,3-dimethylbutyl-, 1,1,2-trimethylpropyl-, 1,2,2-trimethylpropyl-, 1-ethylbutyl-, 1-ethyl-2-methylpropyl-, n-heptyl-, 2-heptyl-, 3-heptyl-, 2-ethylpentyl-, 1-propylbutyl-, n-octyl-, 2-ethylhexyl-, 2-propylheptyl-, nonyl-, decyl.

The elucidations relating to the expression "—($C_1$-$C_{12}$)-alkyl" also apply to the alkyl groups in —O—($C_1$-$C_{12}$)-alkyl, i.e. in —($C_1$-$C_{12}$)-alkoxy. Preferably, these groups are unsubstituted straight-chain or branched —($C_1$-$C_8$)-alkoxy groups.

Substituted —($C_1$-$C_{12}$)-alkyl groups and substituted —($C_1$-$C_{12}$)-alkoxy groups may have one or more substituents, depending on their chain length. The substituents are preferably each independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl and alkoxycarbonyl.

The expression "—($C_3$-$C_{12}$)-cycloalkyl", in the context of the present invention, encompasses mono-, bi- or tricyclic hydrocarbyl radicals having 3 to 12, especially 5 to 12, carbon atoms. These include cyclopropyl-, cyclobutyl-, cyclopentyl-, cyclohexyl-, cycloheptyl-, cyclooctyl-, cyclododecyl-, cyclopentadecyl-, norbonyl- and adamantyl.

The expression "—($C_3$-$C_{12}$)-heterocycloalkyl groups", in the context of the present invention, encompasses nonaromatic saturated or partly unsaturated cycloaliphatic groups having 3 to 12, especially 5 to 12, carbon atoms. The —($C_3$-$C_{12}$)-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —($C_3$-$C_{12}$)-heterocycloalkyl groups are tetrahydrothiophenyl, tetrahydrofuryl, tetrahydropyranyl and dioxanyl.

Substituted —($C_3$-$C_{12}$)-cycloalkyl groups and substituted —($C_3$-$C_{12}$)-heterocycloalkyl groups may have one or more (e.g. 1, 2, 3, 4 or 5) further substituents, depending on their ring size. These substituents are preferably each independently selected from —($C_1$-$C_{12}$)-alkyl, —($C_1$-$C_{12}$)-alkoxy, —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl and alkoxycarbonyl. Substituted —($C_3$-$C_{12}$)-cycloalkyl groups preferably bear one or more —($C_1$-$C_6$)-alkyl groups. Substituted —($C_3$-$C_{12}$)-heterocycloalkyl groups preferably bear one or more —($C_1$-$C_6$)-alkyl groups.

In the context of the present invention, the expression "—($C_6$-$C_{20}$)-aryl" encompasses mono- or polycyclic aromatic hydrocarbyl radicals. These have 6 to 20 ring atoms, more preferably 6 to 14 ring atoms, especially 6 to 10 ring atoms. Aryl is preferably —($C_6$-$C_{10}$)-aryl. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —($C_6$-$C_{20}$)-aryl groups may have one or more (e.g. 1, 2, 3, 4 or 5) substituents, depending on the ring size. These substituents are preferably each independently selected from —($C_1$-$C_{12}$)-alkyl, —($C_1$-$C_{12}$)-alkoxy, —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl and alkoxycarbonyl.

Substituted —($C_6$-$C_{20}$)-aryl groups are preferably substituted —($C_6$-$C_{10}$)-aryl groups, especially substituted phenyl or substituted naphthyl or substituted anthracenyl. Substituted —($C_6$-$C_{20}$)-aryl groups preferably bear one or more, for example 1, 2, 3, 4 or 5, substituents selected from —($C_1$-$C_{12}$)-alkyl groups, —($C_1$-$C_{12}$)-alkoxy groups.

In one variant of the process, it comprises the additional process step of:

b) introducing the first solution into a second solution comprising a second solvent selected from aromatics, $C_5$-$C_{10}$-alkanes, alcohols, acetone, ethyl acetate, acetonitrile, ether, water.

In one variant of the process, the first solution comprises dimethytaminobutane.

In one variant of the process, the first solvent is selected from: ethyl acetate, anisole, ortho-xylene, toluene, acetone, methanol, ethanol, propanol, isopropanol, acetonitrile, water.

Preferably, the first solvent is selected from: ethyl acetate, anisole, ortho-xylene, toluene, water.

More preferably, the first solvent is toluene.

In one variant of the process, the second solvent is selected from:

ethyl acetate, anisole, ortho-xylene, toluene, acetone, methanol, ethanol, propanol, isopropanol, acetonitrile, tetrahydrofuran, diethyl ether, glycol, $C_5$-$C_{10}$-alkanes, water.

Preferably, the second solvent is selected from: ethyl acetate, acetone, methanol, ethanol, propanol, isopropanol, acetonitrile, $C_5$-$C_{10}$-alkanes.

More preferably, the second solvent is acetonitrile.

In one variant of the process, the second solution comprises dimethylaminobutane or triethylamine.

In one variant of the process, the second solution comprises dimethylaminobutane.

In one variant of the process, in process step a), the organomonophosphite is dissolved fully in the first solution.

In one variant of the process, the introduction in process step b) is effected by means of dropwise addition.

In another variant of the process, the introduction in process step b) is effected by means of metered addition.

In one variant of the process, the purified organomonophosphite has a chlorine content of <1000 ppm.

In one variant of the process, the purified organomonophosphite has a chlorine content of <100 ppm.

In one variant of the process, the organomonophosphite has a chlorine content of 1500 ppm to 100 000 ppm on introduction in process step b).

Preferably, the organomonophosphite has a chlorine content of 5000 ppm to 100 000 ppm on introduction in process step b).

The chlorine contents reported are meant as total chlorine contents.

The total chlorine content is determined by the Wickbold method: sample preparation according to DIN 51408 and measurement by ion chromatography according to DIN EN ISO 10304.

In one variant of the process, the second solution is heated to a temperature in the range from −20° C. to 120° C. before the first solution is introduced into the second solution in process step b). The temperature of the solvent should be chosen here such that it does not boil. The temperature thus depends on the choice of solvent.

Preferably, the second solution is brought to a temperature in the range from −10° C. to 80° C. before the first solution is introduced into the second solution in process step b).

In one variant of the process, the organomonophosphite has one of the general formulae I, II, III and IV:

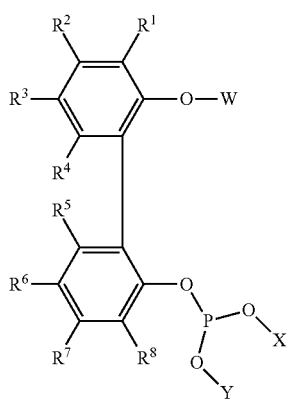
(I)

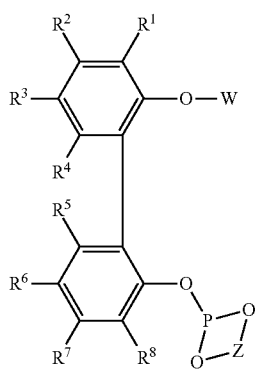
(II)

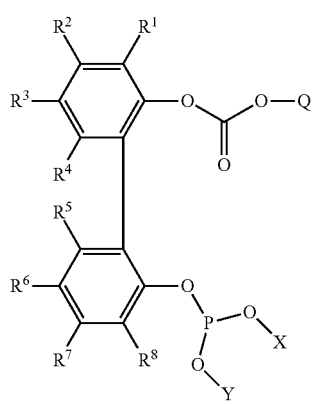
(III)

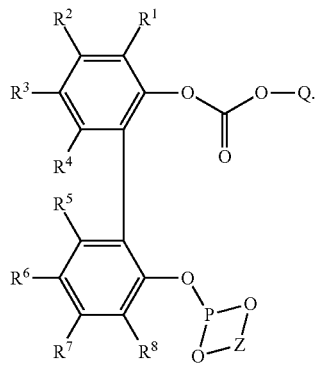
(IV)

In one variant of the process, $R^1$, $R^2$, $R^3$, $R^4$, $R^5$, $R^6$, $R^7$, $R^8$ are each independently selected from: —H, —($C_1$-$C_{12}$)-alkyl, —O—($C_1$-$C_{12}$)-alkyl, —O—($C_6$-$C_{20}$)-aryl, —($C_6$-$C_{20}$)-aryl.

and W is —$CH_3$;
and Q is —$C(CH_3)_3$.

In one variant of the process, Z is:

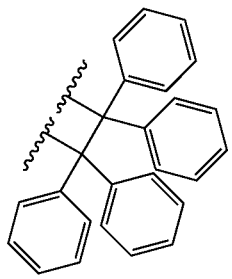 [SMILES: *C(c1ccccc1)(c1ccccc1)C(*)(c1ccccc1)c1ccccc1]

In one variant of the process, Z is:

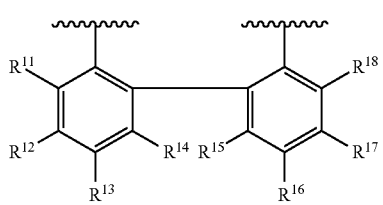

where $R^{11}$, $R^{12}$, $R^{13}$, $R^{14}$, $R^{15}$, $R^{16}$, $R^{17}$, $R^{18}$ are each independently selected from:
—H, —($C_1$-$C_{12}$)-alkyl, —O—($C_1$-$C_{12}$)-alkyl, —O—($C_6$-$C_{20}$)-aryl. —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —$SO_3H$, —$SO_3Na$, —$NO_2$, —CN, —$NH_2$, —N[($C_1$-$C_{12}$)-alkyl]$_2$.

In one variant of the process, the radicals $R^{11}$, $R^{12}$, $R^{13}$, $R^{14}$, $R^{15}$, $R^{16}$, $R^{17}$, $R^{18}$ are each independently selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br. I).

In one variant of the process, the radicals $R^{11}$, $R^{12}$, $R^{13}$, $R^{14}$, $R^{15}$, $R^{16}$, $R^{17}$, $R^{18}$ are each independently selected from:
—H, —($C_1$-$C_{12}$)-alkyl, —O—($C_1$-$C_{12}$)-alkyl.

The process of the invention serves with particular preference for the purification of monophosphites of one of the structural formulae XI, XII, XIII, XIV, XV and XVI:

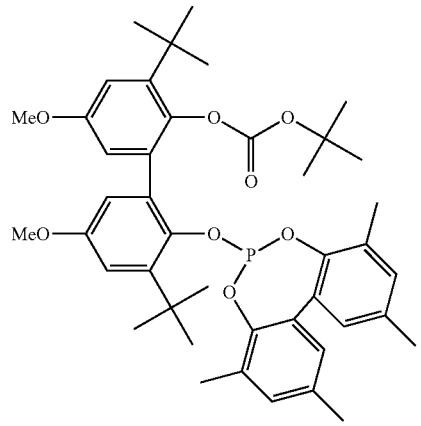
(XI)

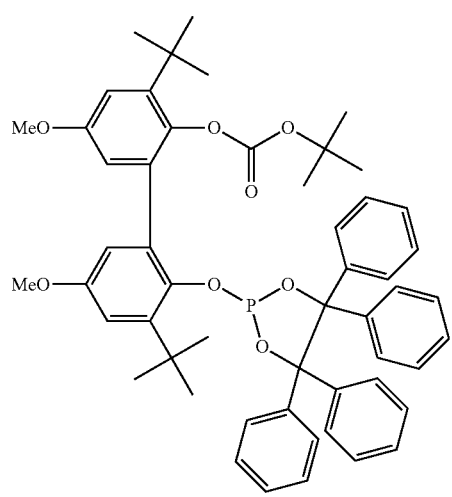
(XII)

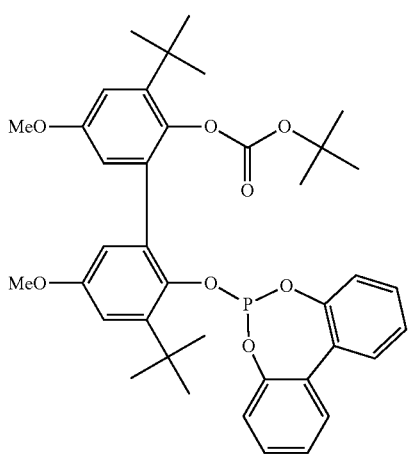
(XIII)

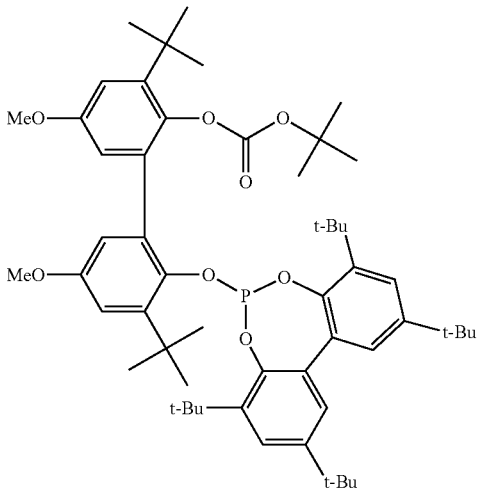
(XIV)

(XV)

(XVI)

The process claimed may also have upstream process steps, for example the synthesis of the ligands. In that case, these process steps are effected prior to process step a).

Where the ligand is synthesized upstream of process step a), the organomonophosphite may be isolated after crystallization has taken place. This is typically accomplished by filtering off and, optionally, drying the filtered-off organomonophosphite.

A particular advantage is that certain solvent combinations which result from the ligand synthesis (acetonitrile (ACN), N,N'-dimethylaminobutane (DMAB) or triethylamine (NEt₃)) can be used for recrystallization after a single distillation.

This allows reuse of the mixture used from the synthesis, which is advantageous from an ecological and economic point of view. Furthermore, it is also possible to dispense with the addition of a filtration aid.

This is therefore a particularly simple and efficient process. In this context, it is also particularly advantageous that this process is performable very rapidly, meaning that the purified organomonophosphite precipitates out or crystallizes out again after a short reaction time, and the process thus has good space-time yields. This is advantageous especially for a synthesis on the industrial scale, since prolonged reaction times directly affect the cost of the compound. The good possibility of industrial scale use is an important criterion, since the preparation complexity and the associated costs that arise may only be so high that the viability of the overall process is still assured.

As well as the process, the use of the product obtained by this process in a hydroformylation reaction is also claimed. The product here functions as a ligand in a catalyst complex composed of the ligand and at least one central metal atom or ion. This catalyst complex is used for catalysis of a hydroformylation reaction.

The use of an organomonophosphite of one of the general formulae I, II, IV, N, V, VI, VII, VIII, IX and X which has been purified by an above-described method as a ligand in a catalyst complex which catalyzes a hydroformylation reaction.

The invention is to be illustrated in detail hereinafter by working examples.

General Operating Procedures

The total chlorine content reported in connection with this invention is determined according to Wickbold: Sample preparation according to DIN 51408 and measurement by ion chromatography according to DIN EN ISO 10304.

All the preparations which follow were conducted with standard Schlenk vessel technology under protective gas. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

The products were characterized by means of NMR spectroscopy. Chemical shifts are reported in ppm.

The $^{31}$P NMR signals were referenced according to: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84). The chlorine determination was effected in the form of combustion according to Wickbold; with sample preparation to DIN 51408 and analysis by ion chromatography to DIN EN ISO 10304.

EXAMPLE 1

: Synthesis of (XI)

Reaction Scheme

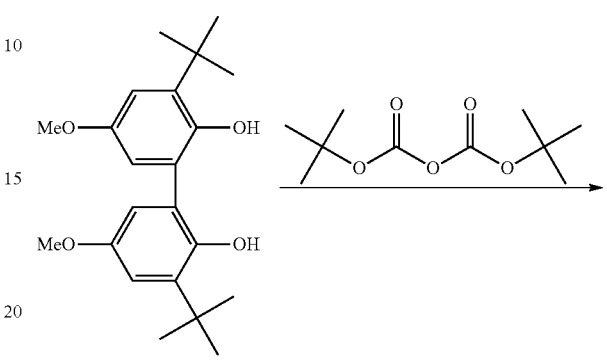

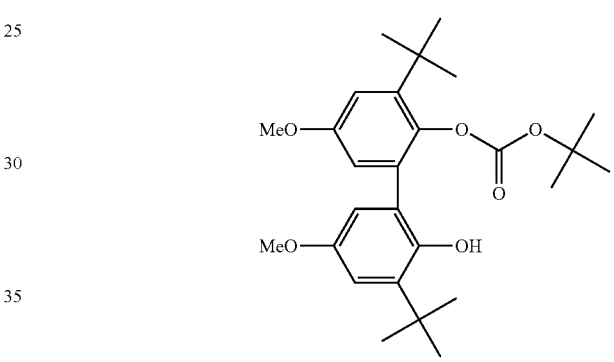

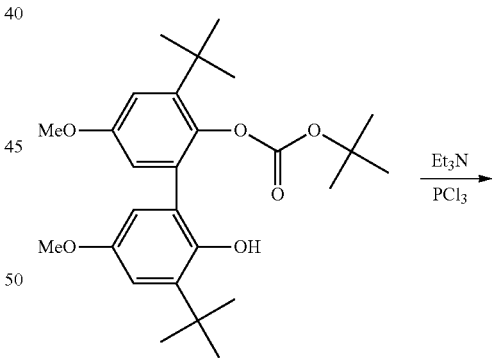

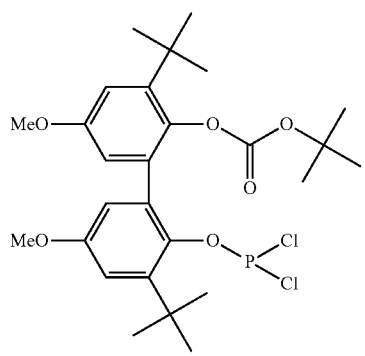

-continued

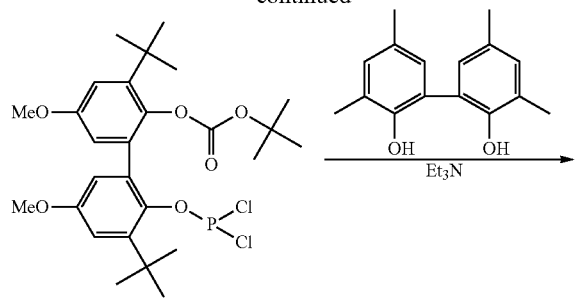

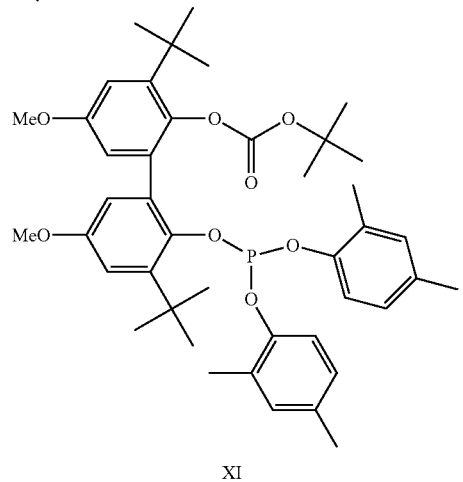

Introduction of the BOC Group:

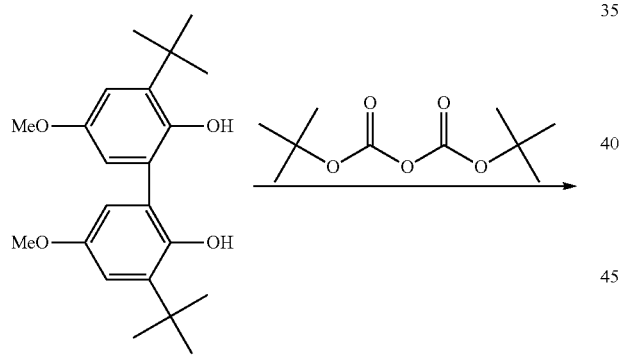

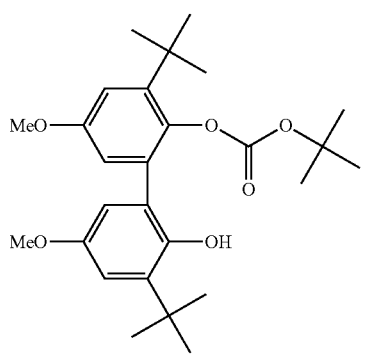

In a 2 l Schlenk flask, 400 mmol (143.8 g) of 3,3'-di-tert-butyl-5,5'-dimethoxy-(1,1'-biphenyl-2,2'-diol and 40 mmol (4.8 g) of N,N-dimethylaminopyridine (DMAP) were dissolved in 900 ml of $CH_2Cl_2$. Subsequently, at room temperature, 400 mmol (88 g) of di-tert-butyl dicarbonate were dissolved in 280 ml of $CH_2Cl_2$, transferred to a 500 ml dropping funnel and added dropwise to the biphenol/DMAP solution at 32° C. within one hour. The solution was stirred at room temperature overnight. The next morning, the solvent was removed under reduced pressure. The slightly waxy, reddish residue was admixed with 800 ml of n-heptane and stirred overnight. This gave a white residue which was filtered off, washed twice with 50 ml of n-heptane and then dried. The target product was obtained as a white solid (161.6 g, 84%). $^1H$ NMR (toluene-$d_8$): 95% and further impurities.

Reaction of tert-butyl (3,3'-di-tert-butyl-2'-hydroxy-5,5'-dimethoxy-[1,1'-biphenyl]-2-yl)carbonate with phosphorus trichloride

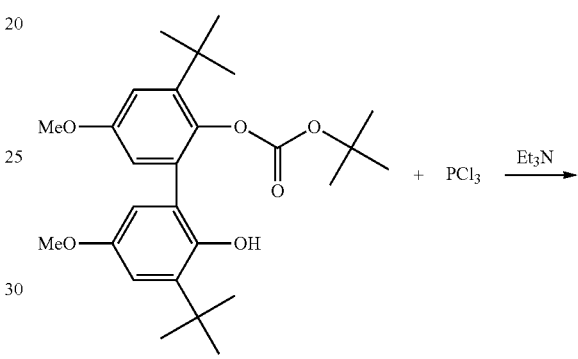

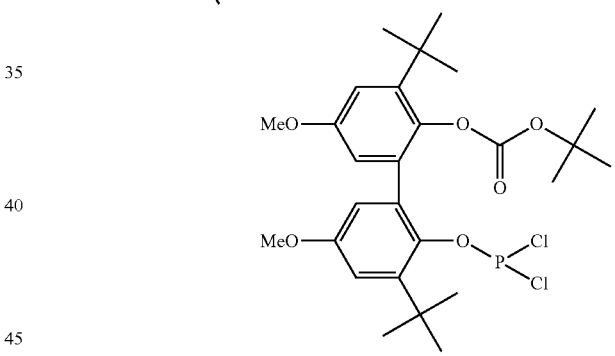

In a 250 ml Schlenk flask which had been repeatedly evacuated and filled with inert gas, 12 g (0.026 mol) of tert-butyl (3,3'-di-tert-butyl-2'-hydroxy-5,5'-dimethoxy-[1,1'-biphenyl]-2-yl)carbonate were dissolved by stirring in 120 ml of dried toluene and 12.8 ml (0.091 mol) of triethylamine.

In a second 500 ml Schlenk flask, 100 ml of dried toluene were first stirred together with 8.1 ml (0.091 mol) of phosphorus trichloride. Subsequently, the phosphorus trichloride-toluene solution was added dropwise to the previously prepared carbonate-amine-toluene solution at room temperature within 30 minutes. On completion of addition, the mixture was heated to 80° C. for 30 minutes and cooled to RT overnight.

The next morning, the mixture was filtered, the solids were washed with 50 ml of dried toluene, and the filtrate was concentrated to dryness. The target product was obtained as a solid (13.1 g, 89%). $^{31}P$ NMR (202.4 MHz, toluene-$d_8$): 203.2 and 203.3 ppm (100%).

Reaction of tert-butyl (3,3'-di-tert-butyl-2'-((dichlorophosphino)oxy)-5,5'-dimethoxy-[1,1'-biphenyl]-2-yl)carbonate with 3,3',5,5'-tetramethyl-(1,1'-biphenyl)-2,2'-diol

EXAMPLE 2

Synthesis of (XII)

Reaction of ter-butyl (3,3'-di-tert-butyl-2'-hydroxy-5,5'-dimethoxy-[1,1'-biphenyl]-2-yl)carbonate with 2-chloro-4,4,5,5-tetraphenyl-1,3,2-dioxaphospholane

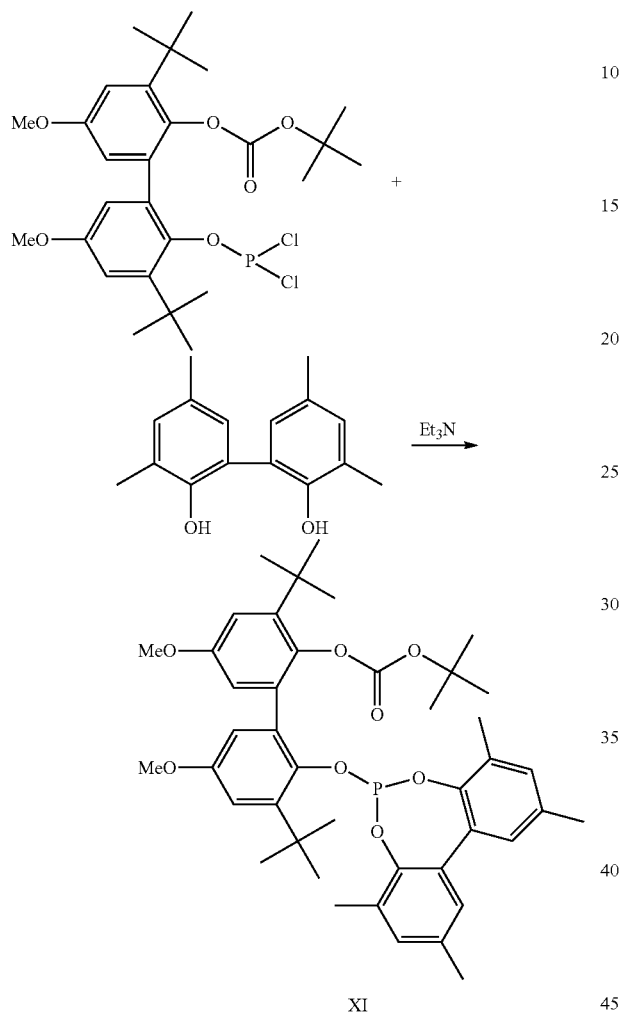

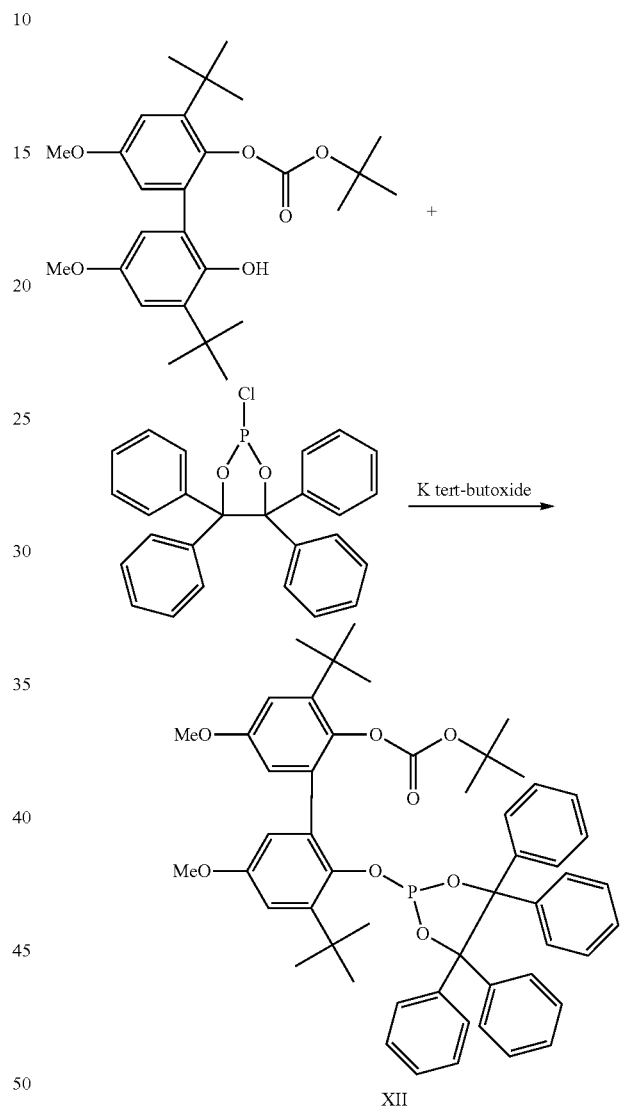

In a 1 l Schlenk flask which had been repeatedly evacuated and filled with inert gas, 24.7 g (0.044 mol) of tert-butyl (3,3'-di-tert-butyl-2'-((dichlorophosphino)oxy)-5,5'-dimethoxy-[1,1'-biphenyl]-2-yl)carbonate were dissolved in 400 ml of acetonitrile.

In a second Schlenk flask (1 l) which had been repeatedly evacuated and filled with inert gas, 10.8 g (0.044 mol) of 3,3',5,5'-tetramethyl-(1,1'-biphenyl)-2,2'-diol were dissolved by stirring in 200 ml of acetonitrile and 13.1 ml (0.011 mol) of dried triethylamine. Subsequently, the chlorophosphite solution was slowly added dropwise to the biphenol-triethylamine solution and the mixture was stirred overnight.

The mixture was then filtered and the residue was washed twice with 15 ml of acetonitrile.

The filtrate was concentrated under reduced pressure until a solid precipitated out. The latter was filtered and dried. The target product (XI) was obtained as a white solid (28.5 g, 87%). $^{31}P$ NMR (202.4 MHz, toluene-$d_8$): 139.4 ppm (98.5%).

In a 250 ml Schlenk flask which had been repeatedly evacuated and filled with inert gas, 9.1 g (0.021 mol) of 2-chloro-4,4,5,5-tetraphenyl-1,3,2-dioxaphospholane were dissolved in 75 ml of dried toluene.

In a second Schlenk flask (250 ml), 9.2 g (0.02 mol) of tert-butyl (3,3'-di-tert-butyl-2'-hydroxy-5,5'-dimethoxy-[1,1'-biphenyl]-2-yl)carbonate and 2.3 g (0.02 mol) of potassium tert-butoxide were dissolved in 75 ml of dried toluene while stirring.

Subsequently, the carbonate/potassium tert-butoxide/toluene mixture was slowly added dropwise at room temperature to the chlorophosphite solution, and the mixture was stirred at room temperature overnight.

Thereafter, the solvent was removed under reduced pressure. The resultant residue was stirred in 75 ml of dried acetonitrile for 5 hours. The solids were filtered, washed with dried acetonitrile and dried. The target product (XII) was obtained as a white solid (15.3 g, 90%). $^{31}$P NMR (202.4 MHz, toluene-$d_8$): 147.0 ppm (99%).

EXAMPLE 3

Synthesis of (XIII)

Reaction of tert-butyl (3,3'-di-tert-butyl-2'-((dichlorophosphino)oxy)-5,5'-dimethoxy-[1,1'-biphenyl]-2-yl)carbonate with 2,2'-biphenol

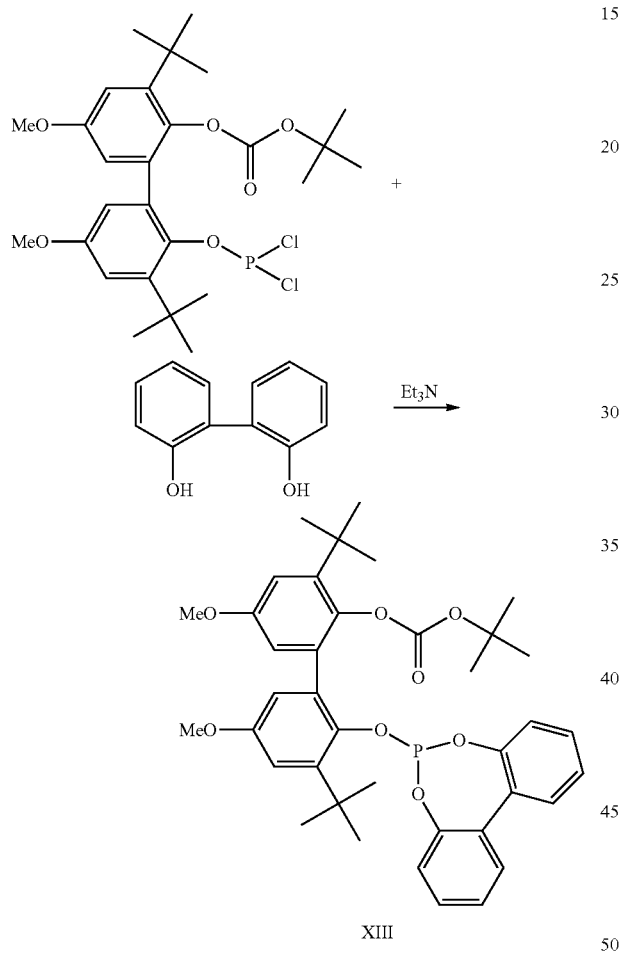

EXAMPLE 4

Synthesis of (XIV)

Reaction of tert-butyl (3,3'-di-tert-butyl-2'-((dichlorophosphino)oxy)-5,5'-dimethoxy-[1,1'-biphenyl]-2-yl)carbonate with 3,3,5,5-tetra-tert-butylbiphenol

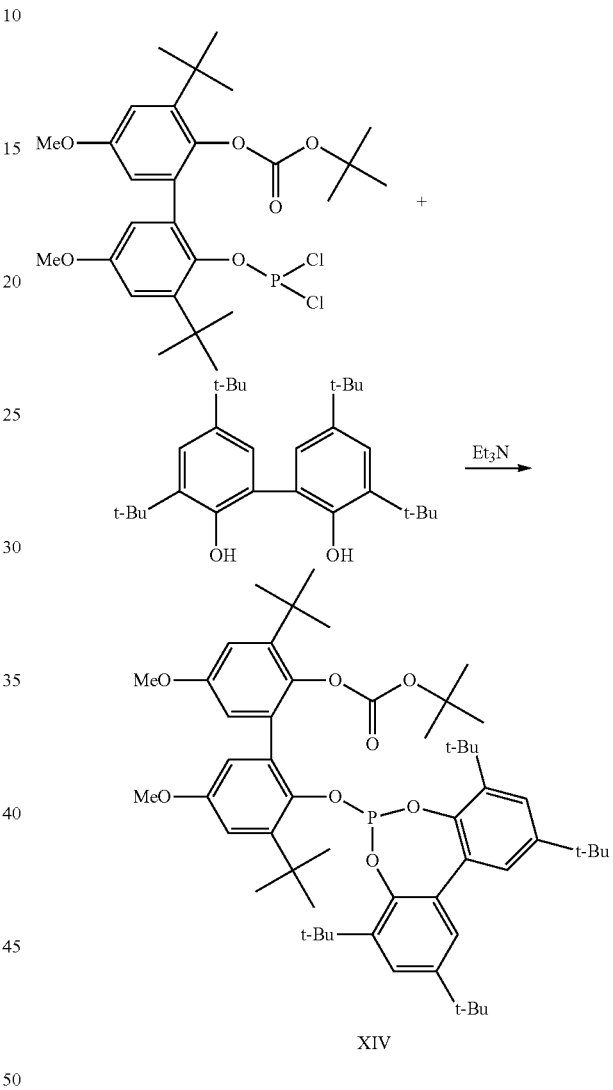

In a 250 ml Schlenk flask which had been repeatedly evacuated and filled with inert gas, 10.5 g (0.019 mol) of tert-butyl (3,3'-di-tert-butyl-2'-((dichlorophosphino)oxy)-5,5'-dimethoxy-[1,1'-biphenyl]-2-yl)carbonate were dissolved in 50 ml of degassed acetonitrile while stirring.

In a second Schlenk flask (250 ml) which had been repeatedly evacuated and filled with inert gas, 3.6 g (0.019 mol) of 2,2'-biphenol were dissolved in 40 ml of degassed acetonitrile and 6.3 ml (0.045 mol) of dried triethylamine while stirring. Subsequently, the chlorophosphite mixture was slowly added dropwise at room temperature to the biphenol/triethylamine solution, and the mixture was stirred at room temperature overnight. The resultant solids were filtered and dried. The target product (XIII) was obtained as a white solid (11.5 g, 90%). $^{31}$P NMR (202.4 MHz, toluene-$d_8$): 146.2 ppm (100%).

In a 250 ml Schlenk flask which had been repeatedly evacuated and filled with inert gas, 7.0 g (0.0125 mol) of tert-butyl (3,3'-di-tert-butyl-2'-((dichlorophosphino)oxy)-5,5'-dimethoxy-[1,1'-biphenyl]-2-yl)carbonate were dissolved in 100 ml of dried acetonitrile.

In a second Schlenk flask (100 ml) which had been repeatedly evacuated and filled with inert gas, 5.1 g (0.0125 mol) of 3,3',5,5'-tetra-tert-butylbiphenol were dissolved in 60 ml of dried acetonitrile and 4.2 ml (0.03 mol) of dried triethylamine while stirring. Subsequently, the biphenol-triethylamine solution was slowly added dropwise at room temperature to the chlorophosphite solution and the mixture was stirred overnight. A portion of the solvent was removed under reduced pressure. The precipitated solids were filtered off and dried. The target product (XIV) was obtained as a white solid (10.2 g, 91%). $^{31}$P NMR (202.4 MHz, toluene-$d_8$): 142.7 ppm (100%).

EXAMPLE 5

Synthesis of (XV)

Reaction of tert-butyl (3,3'-di-tert-butyl-2'-(dichlorophosphino)oxy)-5,5'-dimethoxy-[1,1'-biphenyl]-2-yl)carbonate with 3,3-di-tert-butyl-5,5-dimethoxybiphenol

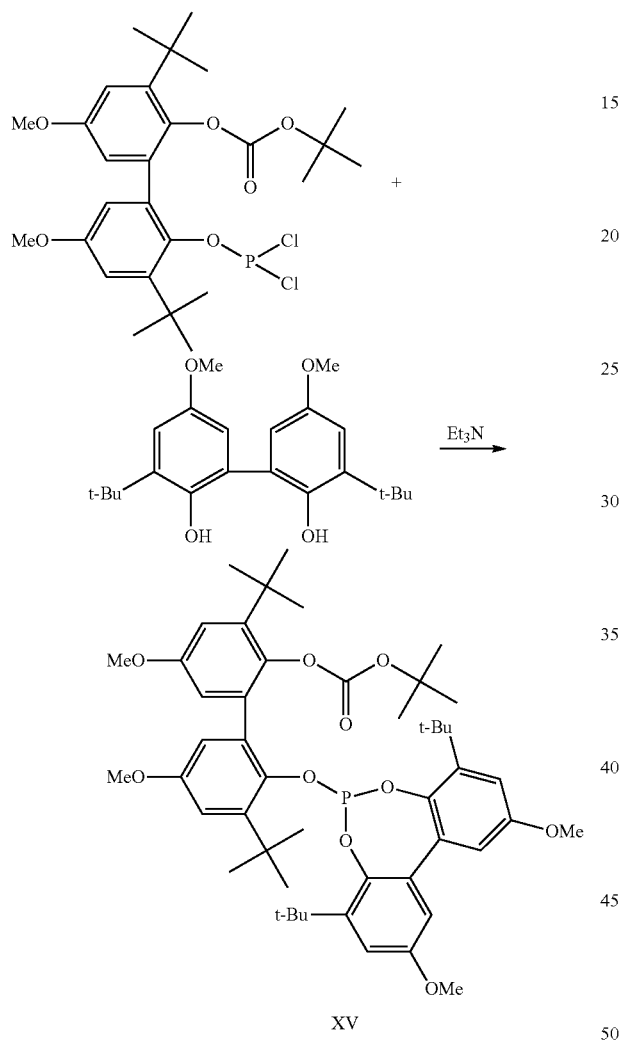

XV

In a 250 ml Schlenk flask which had been repeatedly evacuated and filled with inert gas, 7 g (0.0125 mol) of tert-butyl (3,3'-di-tert-butyl-2'-(dichlorophosphino)oxy)-5,5'-dimethoxy-[1,1'-biphenyl]-2-yl)carbonate were dissolved in 100 ml of dried acetonitrile.

In a second Schlenk flask (100 ml) which had been repeatedly evacuated and filled with inert gas, 4.5 g (0.0125 mol) of 3,3-di-tert-butyl-5,5-dimethoxybiphenol were dissolved in 60 ml of dried acetonitrile and 4.2 ml (0.03 mol) of degassed triethylamine. Subsequently, the biphenol-triethylamine solution was slowly added dropwise at 40° C. to the chlorophosphite solution, and the reaction mixture was heated to 80° C. and stirred at this temperature for 6 h. This was followed by hot filtration.

A portion of the solvent was removed under reduced pressure. The precipitated solids were filtered off and dried.

The target product (XV) was obtained as a white solid (10.5 g, 96%). $^{31}$P NMR (202.4 MHz, toluene-$d_8$): 140.9 ppm (95.2%) and further impurities (further impurities=P—H compounds, oxide compounds, as yet incompletely converted chlorophosphite).

EXAMPLE 6

Synthesis of (XVI)

Reaction of tert-butyl (3,3-di-tert -2'-((dichlorophosphino)oxy)-5,5'-dimethoxy-[1,1'-biphenyl]-2-yl) carbonate with 2,4-dimethylphenol

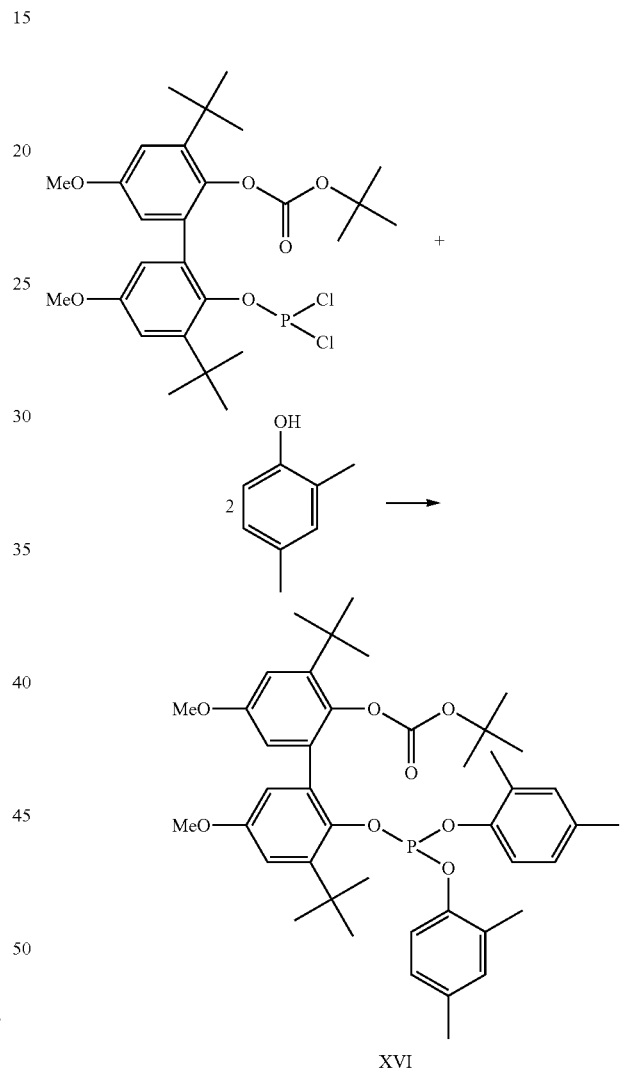

XVI

In a 500 ml Schlenk flask which had been repeatedly evacuated and filled with inert gas, 6.8 g (0.012 mol) of tert-butyl (3,3'-di-tert-butyl-2'-((dichlorophosphino)oxy)-5,5'-dimethoxy-[1,1'-biphenyl]-2-yl)carbonate were dissolved in 100 ml of dried acetonitrile.

In a second Schlenk flask (250 ml) which had been repeatedly evacuated and filled with inert gas, 6 g (6 ml; 0.048 mol) of 2,4-dimethylphenol were dissolved in 100 ml of dried acetonitrile and 5 g (7 ml; 0.059 mol) of degassed triethylamine. Subsequently, the biphenol-triethylamine solution was slowly added dropwise at room temperature to the chlorophosphite solution and the mixture was stirred at room temperature overnight and cooled in an ice bath the next morning.

A portion of the solvent was removed under reduced pressure. This formed a slime-like solution which solidified after prolonged drying. The target product (XVI) was obtained as a white solid (11.8 g, 62%). $^{31}$P NMR (202.4 MHz, toluene-d$_8$): 139.1 ppm (92.8%) and further impurities (further impurities=P—H compounds, oxide compounds, as yet incompletely converted chlorophosphite).

EXAMPLE 7

Synthesis of bis(2,4-di-tert-butyl-6-methylphenyl)ethyl phosphate

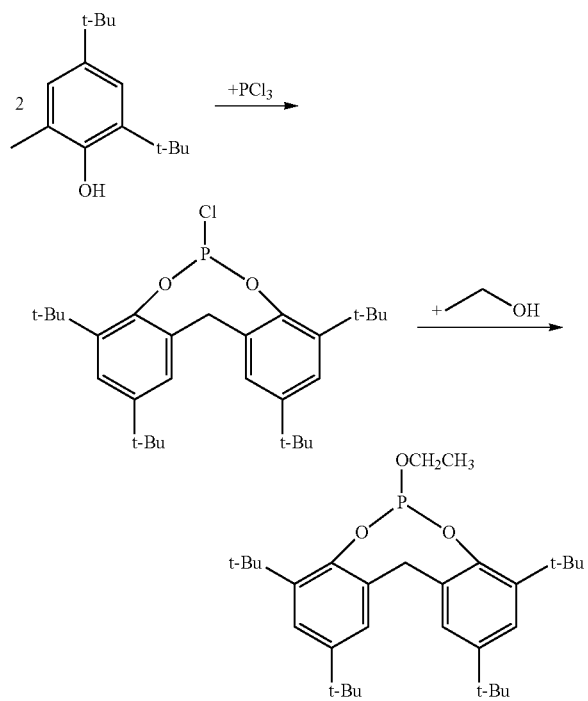

A 250 ml Schlenk flask with magnetic stirrer, attachment, dropping funnel and reflux condenser was initially charged with 22.5 g (0.1 mol) of 2,4-di-tert-butyl-6-methylphenol (4,6-di-tert-butyl-ortho-cresol), and heated to 55° C. in order to melt the phenol. 0.13 ml (0.0015 mol) of dried degassed dimethylformamide was added to the melt. Subsequently, 5.7 ml (0.065 mol) of phosphorus trichloride were added dropwise within 2 hours. After the addition had ended, the reaction mixture was heated to 140° C. within 3 hours and stirred at this temperature for 1 hour. Then the mixture was stirred at 130° C. under reduced pressure for 1 hour. Thereafter, the clear yellow-orange melt obtained (=bis(2,4-di-tert-butyl-6-methyl) phosphochloridite) was cooled down to 80° C. overnight and diluted with 75 ml of degassed petroleum (80-110° C.). After the solution had been cooled down to −5° C., 9.1 ml (0.0665 mol) of degassed triethylamine were added within 15 minutes. Subsequently, within 2 hours, 4.4 ml (0.075 mol) of dried and degassed ethanol were added dropwise, in the course of which the temperature did not rise above 5° C. This mixture was warmed gradually to room temperature overnight while stirring.

The next morning, the precipitated triethylamine hydrochloride was filtered off and the filtrate was concentrated under reduced pressure. This gave a white residue which was recrystallized in 60 ml of degassed ethanol. The product was thus obtained in a yield of 73.9% (19.03 g) as a white solid in 98% purity by LC-MS.

Chlorine Reduction

EXAMPLE 8

Chlorine Reduction of (XI)

a) toluene-DMAB/acetonitrile-DMAB

In a 500 ml Schlenk flask which had been repeatedly evacuated and filled with inert gas, 10 g of crude ligand (XI) having an initial chlorine level of 5.7% by weight were heated to 105° C. in 40 ml of degassed toluene and 10 ml of N,N'-dimethylaminobutane with stirring.

A second 500 ml Schlenk flask which had been repeatedly evacuated and filled with inert gas was initially charged with 90 ml of degassed acetonitrile and 10 ml of N,N'-dimethylaminobutane, while stirring. Thereafter, the ligand/toluene/amine solution was added dropwise at room temperature to the acetonitrile-amine solution while stirring within a couple of minutes. In order to hold back the insoluble solid fraction, dropwise addition took place through a frit.

After the clear solution had been stirred for 12 hours, the solvent was removed under reduced pressure. Thereafter, the resulting solid was admixed with 40 ml of degassed acetonitrile and stirred at room temperature for 12 hours. The mixture was subsequently filtered and dried. The product was obtained in 67% yield (5.9 g).

NMR result: 100% P 139.3 ppm (toluene-d8).

Result of duplicate Wickbold chlorine determination: 65/65 mg/kg (ppm)

For accuracy, the chlorine levels were analyzed in a duplicate determination.

b) toluene-DMAB/acetonitrile

In a 2 l Schlenk vessel which had been repeatedly evacuated and filled with inert gas, 115.6 g of crude ligand (XI) having an initial chlorine level of 5.7% by weight were heated to 105° C. in 460 ml of degassed toluene and 100 ml of N,N'-dimethylaminobutane, with stirring, and stirred at this temperature for about 10 minutes.

For further work-up, the mixture was cooled to room temperature and filtered through a frit.

The resulting filtrate was then concentrated to dryness under reduced pressure. Thereafter, the solid obtained was admixed with 290 ml of degassed acetonitrile, stirred for 15 minutes at 78° C., cooled to room temperature again and stirred at room temperature overnight. In the morning, the solid was filtered off, rinsed with 50 ml of degassed acetonitrile, and dried. The product was obtained in 61.8% yield.

NMR result: 100% P 139.3 ppm (toluene-d8).

Result of duplicate Wickbold chlorine determination: 75/80 mg/kg (ppm)

c) toluene-DMAB/acetonitrile

In a 2 l Schlenk vessel which had been repeatedly evacuated and filled with inert gas, 189.6 g of crude ligand (XI) having an initial chlorine level of 1.1% by weight were heated to 105° C. in 760 ml of degassed toluene and 165 ml of N,N'-dimethylaminobutane, with stirring, and stirred at this temperature for about 10 minutes.

For further work-up, the mixture was cooled to room temperature and filtered through a frit.

The resulting filtrate was then concentrated to dryness under reduced pressure, admixed with 475 ml of degassed acetonitrile, stirred at 75° C. for 15 minutes and then cooled back down to room temperature with stirring overnight. In the morning, the solid was filtered off, rinsed with 50 ml of degassed acetonitrile, and dried.

The product was obtained in 86% yield (160 g).

NMR result: 100% P 139.3 ppm (toluene-d8).

Chlorine result according to Wickbold: <10 mg/kg (ppm)

d) work-up using toluene/methanol/triethanolamine (comparative example)

In a 100 ml Schlenk flask which had been repeatedly evacuated and filled with inert gas, 10.06 g of (XI) having an initial chlorine level of 1.1% by weight were weighed out and admixed with 45 ml of degassed toluene. This suspension was heated to 102° C. and left with stirring for 20 minutes. During this time, the major fraction dissolved. Only a few particles were insoluble. Subsequently, the slightly turbid solution was subjected to hot filtration, and the clear filtrate was concentrated to dryness under reduced pressure at room temperature.

The next morning, 150 ml of degassed methanol and 15 ml of degassed triethanolamine were added to the solid residue from the concentrated filtrate, and stirring was carried out for 3 hours.

This gave a white suspension. The solid was subsequently isolated by filtration and dried.

The product was obtained in 98% yield (9.8 g).

NMR result 100% P 139.3 ppm (toluene-d8).

Chlorine result according to Wickbold: 120 mg/kg (ppm)

EXAMPLE 9

Chlorine Reduction of (XV)

a) work-up using degassed ethanol+1% degassed water+5% degassed DMAB at 0° C.

For work-up, 300 ml of degassed ethanol and 15 ml of degassed N,N'-dimethylaminobutane were initially added with stirring to the crude ligand (XV) with an initial chlorine level of 1.3% and the mixture was stirred for 2 h. Thereafter, 3 ml of degassed DI water were added and the mixture was cooled to 0° C. and stirred for 2 h. The solid was then isolated by filtration, rinsed twice with 40 ml of cold, degassed ethanol, and dried.

Result of duplicate Wickbold chlorine determination: 20/20 mg/kg (ppm)

Yield: 68.01 g corresponding to 68.9%.

b) work-up using water/acetonitrile/N,N'-dimethylaminobutane (10:10:1)

For further work-up, the crude ligand (XV) with an initial chlorine level of 1.3 wt % was dissolved with stirring in 40 ml of degassed ACN and 4 ml of degassed N,N'-dimethylaminobutane (5%).

This was followed by overnight stirring at RT. Initial precipitation was observed after about 1 h. In the morning, 40 ml of degassed DI water were added to the mixture. The mixture was stirred for 30 minutes. Then the solid was isolated by filtration, washed with a little degassed water, and dried.

Result of duplicate Wickbold chlorine determination: 50/55 mg/kg (ppm)

Yield: 16.6 g corresponding to 64.02%.

TABLE 1

Chlorine levels

| | 1st solvent | 1st base | 2nd solvent | 2nd base | Chlorine level, average value [ppm] |
|---|---|---|---|---|---|
| 8a) | toluene | DMAB | acetonitrile | DMAB | 65 |
| 8b) | toluene | DMAB | acetonitrile | | 77.5 |
| 8c) | toluene | DMAB | acetonitrile | | <10 |
| 8d)* | toluene | | methanol | triethanolamine | 120 |
| 9a) | ethanol | DMAB | $H_2O$ | | 20 |
| 9b) | acetonitrile | DMAB | $H_2O$ | | 52.5 |

*comparative example

DMAB: dimethylaminobutane

The examples above show that by virtue of the use dimethylaminobutane it was possible to lower the chlorine level to a value of less than 100 ppm.

The invention claimed is:

1. A process for reducing the chlorine content in an organomonophosphite of one of the general formulae I, II, III, IV, V, VI, VII, VIII, IX and X:

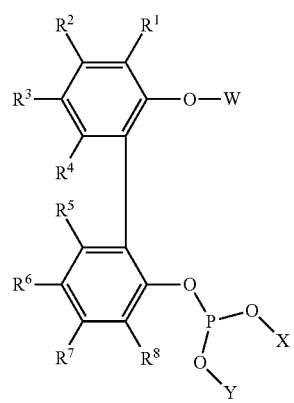

(I)

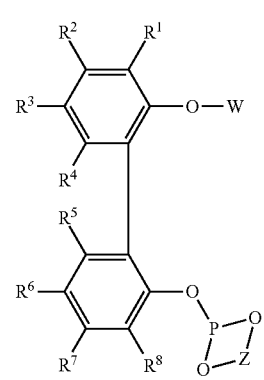

(II)

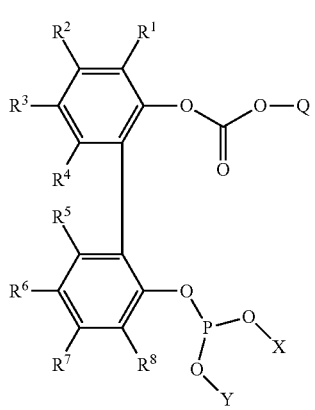
(III)
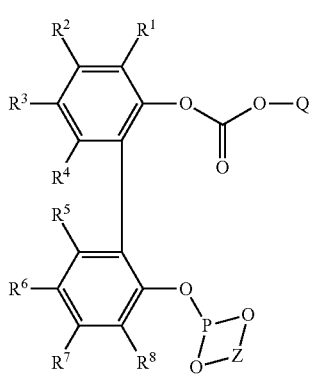
(IV)
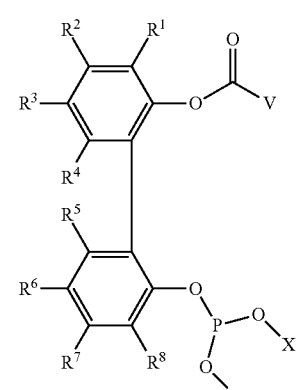
(V)
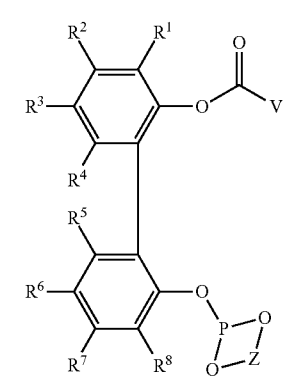
(VI)
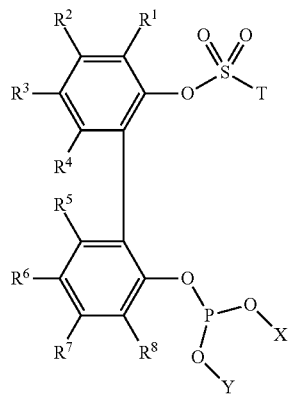
(VII)
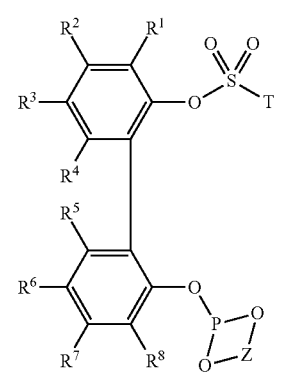
(VIII)
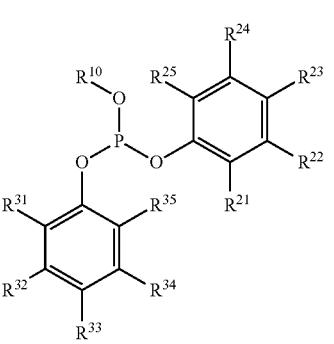
(IX)
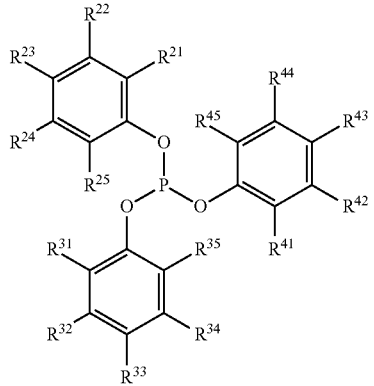
(X)
where the radicals $R^1$, $R^2$, $R^3$, $R^4$, $R^5$, $R^6$, $R^7$, $R^8$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$ and $R^{45}$ are selected each independently from: —H, —$(C_1$-$C_{12})$-alkyl, —O—$(C_1$-$C_{12})$-alkyl, —O—$(C_6$-$C_{20})$-aryl, —$(C_6$-$C_{20})$-aryl, and $R^{10}$ is —$(C_1$-$C_{12})$-alkyl;

and T is selected from:
—CH₃, —CF₃, —CH₂C₆H₅;
and Q is selected from:
—(C₁-C₁₂)-alkyl-, —C(CH₃)₃;
and V is selected from:
—CH₂CH₂COCH₃, —C(CH₃)₃, —CH₆H₅;
and W is selected from:
-Me, —CH₂CH₃, —CH₂CH₂CH₃, —CH₂-cyclo-C₃H₅, —CH(CH₃)₂, -cyclo-C₆H₁₁, —C(CH₃)₃, —CH₂C₆H₅, —CH₂C₆H₃-2,4-(CH₃)₂;
and X and Y are each independently selected from:
—(C₁-C₁₂)-alkyl, —(C₆-C₂₀)-aryl, —(C₆-C₂₀)-aryl-(C₁-C₁₂)-alkyl, —(C₁-C₁₂)-alkyl-(C₆-C₂₀)-aryl;
and Z is selected from:
—(C₁-C₁₂)-alkyl-, —(C₆-C₂₀)-aryl-, —(C₆-C₂₀)-aryl-(C₆-C₂₀)-aryl-;
and the alkyl, cycloalkyl, and aryl groups mentioned may be substituted;
comprising the process steps of:
a) partly or fully dissolving the organomonophosphite in a first solution comprising a first solvent selected from aromatics, alcohols, acetone, ethyl acetate, acetonitrile, ether, water;
where the first solution comprises dimethylaminobutane or triethylamine or triethanolamine;
c) the purified organomonophosphite is precipitated.

2. The process as claimed in claim 1,
which comprises the additional process step of:
b) introducing the first solution into a second solution comprising a second solvent selected from aromatics, $C_5$-$C_{10}$-alkanes, alcohols, acetone, ethyl acetate, acetonitrile, ether, water.

3. The process as claimed in claim 1,
wherein the first solution comprises dimethylaminobutane.

4. The process as claimed in claim 1,
wherein the first solvent is selected from: ethyl acetate, anisole, ortho-xylene, toluene, acetone, methanol, ethanol, propanol, isopropanol, acetonitrile, water.

5. The process as claimed in claim 1,
wherein the first solvent is toluene.

6. The process as claimed in claim 2,
wherein the second solvent is selected from: ethyl acetate, anisole, ortho-xylene, toluene, acetone, methanol, ethanol, propanol, isopropanol, acetonitrile, tetrahydrofuran, diethyl ether, glycol, $C_5$-$C_{10}$-alkanes, water.

7. The process as claimed in claim 2,
wherein the second solvent is acetonitrile.

8. The process as claimed in claim 2,
wherein the second solution comprises dimethylaminobutane or triethylamine.

9. The process as claimed in claim 1,
wherein the organomonophosphite is dissolved fully in the first solution in process step a).

10. The process as claimed in 1,
wherein the purified organomonophosphite has a chlorine content of <200 ppm.

11. The process as claimed in claim 2,
wherein the second solution is brought to a temperature in the range from −10° C. to 80° C. before the first solution is introduced into the second solution in process step b).

12. The process as claimed in claim 1,
wherein the organomonophosphite has one of the general formulae I, II, III and IV:

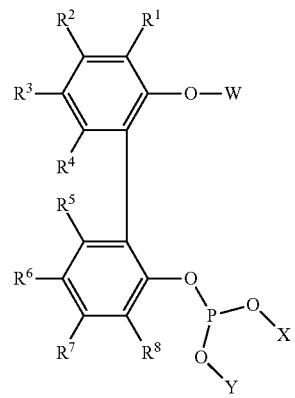

(I)

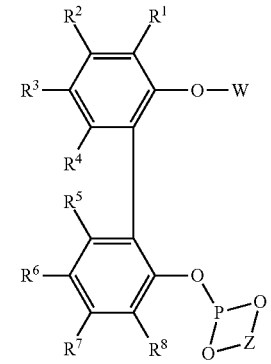

(II)

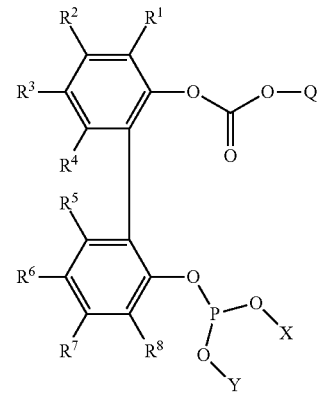

(III)

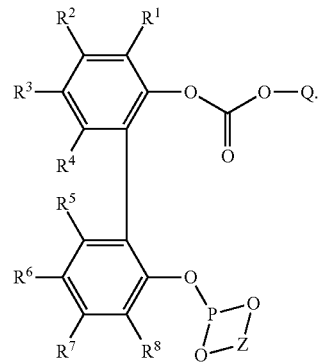

(IV)

13. The process as claimed in claim 1,
wherein
$R^1$, $R^2$, $R^3$, $R^4$, $R^5$, $R^6$, $R^7$, $R^8$ are each independently selected from: —H, —$(C_1$-$C_{12})$-alkyl, —O—$(C_1$-$C_{12})$-alkyl, —O—$(C_6$-$C_{20})$-aryl, —$(C_6$-$C_{20})$-aryl;
and W is —$CH_3$;
and Q is —$C(CH_3)_3$.

14. The process as claimed in claim 1,
where Z is:

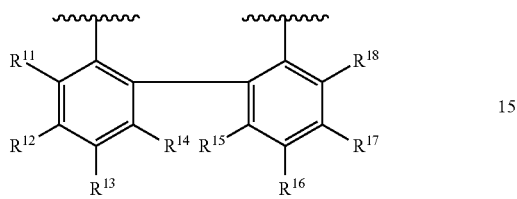

and
where $R^{11}$, $R^{12}$, $R^{13}$, $R^{14}$, $R^{15}$, $R^{16}$, $R^{17}$, $R^{18}$ are each independently selected from:
—H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COON, —OH, —$SO_3H$, —$SO_3Na$, —$NO_2$, —CN, —$NH_2$, —N[$(C_1$-$C_{12})$-alkyl]$_2$.

* * * * *